United States Patent
Harshbarger et al.

(10) Patent No.: US 7,205,497 B2
(45) Date of Patent: Apr. 17, 2007

(54) APPARATUS AND METHOD FOR AUTOMATED PARCEL SCREENING

(75) Inventors: Stuart D. Harshbarger, Woodbine, MD (US); Adam K. Arabian, Louisville, KY (US); Michael P. McLoughlin, Sykesville, MD (US); Micah A. Carlson, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/510,434

(22) PCT Filed: Apr. 16, 2003

(86) PCT No.: PCT/US03/11570

§ 371 (c)(1),
(2), (4) Date: Oct. 6, 2004

(87) PCT Pub. No.: WO03/089156

PCT Pub. Date: Oct. 30, 2003

(65) Prior Publication Data

US 2005/0211606 A1    Sep. 29, 2005

Related U.S. Application Data

(60) Provisional application No. 60/421,301, filed on Oct. 25, 2002, provisional application No. 60/373,003, filed on Apr. 16, 2002.

(51) Int. Cl.
*G06K 9/00* (2006.01)

(52) U.S. Cl. .................. 209/576; 209/900; 382/101

(58) Field of Classification Search ............... 209/576, 209/577, 579, 583, 589, 900, 939; 382/101
See application file for complete search history.

(56) References Cited

U.S. PATENT DOCUMENTS

| 6,573,836 B1 | 6/2003 | Gitis et al. |
| 2002/0124664 A1 | 9/2002 | Call et al. |
| 2003/0113230 A1 | 6/2003 | Cordery et al. |
| 2003/0115998 A1 | 6/2003 | Belec et al. |
| 2003/0119175 A1 | 6/2003 | Stradley et al. |
| 2003/0121839 A1 | 7/2003 | Ryan, Jr. et al. |
| 2003/0136203 A1 | 7/2003 | Yoon |
| 2004/0020264 A1* | 2/2004 | Megerle ................. 73/19.01 |

* cited by examiner

*Primary Examiner*—Joseph C. Rodriguez
(74) *Attorney, Agent, or Firm*—Francis A. Cooch (57) ABSTRACT

A system and method (FIG. 1) for automated handling and identification of parcels sorted by an automated high-speed mail sorting apparatus that identifies parcels that contain hoax or biological threat material comprising an opener (120) and a particle sampler (170) wherein said sampler analyzes air flow created as the parcels are compressed by pinch rollers (140).

6 Claims, 5 Drawing Sheets

APPARATUS AND METHOD FOR AUTOMATED PARCEL SCREENING

CROSS-REFERENCE TO RELATED APPLICATIONS

This application claims the benefit of Provisional Application Ser. No. 60/373,003 entitled "DETECTION OF GENUINE AND HOAX BIOLOGICAL AND NON-BIOLOGICAL CONTAMINANTS ON VARIOUS MEDIA", filed on Apr. 16, 2002, and to Provisional Application Ser. No. 60/421,301 entitled "SYSTEM FOR DETECTION AND IDENTIFICATION OF BIOLOGICAL OR CHEMICAL THREATS IN AUTOMATED MAIL SORTING APPLICATIONS" filed on Oct. 25, 2002, the contents of which are incorporated herein by reference.

STATEMENT OF GOVERNMENTAL INTEREST

This invention was made with Government support under Contract No. N00024-98-D-8124 awarded by the Department of the Navy. The Government has certain rights in this invention.

BACKGROUND OF THE INVENTION

1. Field of the Invention

The invention generally relates to systems for high-speed automated handling and screening of parcels to detect contamination, and applications thereof.

2. Description of the Related Art

Numerous types of high-speed parcel handling systems have been developed and are in use. The United States Postal Service (USPS) and other entities utilize such systems to handle the enormous quantity of parcels that the are received, sorted and delivered each day. A notable feature, and an inherent disadvantage, of the such systems is that the sender of a parcel can remain anonymous.

Following the terrorist attacks of Sep. 11, 2001, the U.S. mail was utilized to propagate bioterrorist attacks upon high level governmental representatives and important members of the media. A number of similar hoax attacks have followed and continue to this day. The ability of the sender of a parcel to remain anonymous has thwarted law enforcement efforts to apprehend the bioterrorist(s).

The need for an apparatus and method for sanitizing parcels that may contain contaminant particles, i.e. anthrax, non-biological contaminant or other particulate matter or hoax contaminant powders, that have the ability to become airborne, has become apparent. The overwhelming volume of parcels handled each day, however, has made it impossible to sanitize every parcel that is delivered. Nonetheless, following the bioterrorist attacks, the USPS began a campaign of irradiating parcels sent to persons and organizations that are likely terrorist targets.

Irradiation, however, is recognized as being an inadequate long-term defense. Aside from entailing an unduly long time to irradiate parcels, the double-digit kilogray doses that are needed to kill anthrax spores makes paper contained within the parcels brittle and smelly, and is fatal to film, magnetic media, electronic devices and prescription drugs that are in the parcels that pass through the irradiating machines. The irradiation has also led to reports of sickness of the workers at the mail processing facilities.

A further shortcoming is that irradiation simply kills the contaminant, and does nothing to identify contaminated parcels. Identification of contaminated parcels is an essential threshold requirement for law enforcement to identify and apprehend the terrorists.

Other techniques that can be used to sanitize suspect parcels include the use of penetrative gamma rays or chemical sterilization, such as by use of chlorine dioxide gas. Each technique has its drawbacks. Use of penetrative gamma rays raises concerns of housing radioactive gamma sources such as cobalt-60, and chlorine dioxide gas requires lengthy exposure time for adequate penetration of the parcels.

The techniques and apparatus known in the art either require individual treatment of the parcels or require prolonged exposure to the sterilization method. Further, known techniques and apparatus fail to identify parcels containing hoax threat materials. Further still, the known techniques and apparatus fail to identify suspect parcels, as necessary to advance the efforts of authorities to apprehend the terrorists and hoax perpetrators.

While known techniques can sanitize parcels, the known techniques fail to screen suspect parcels and cause an unacceptable processing delay of such parcels. Such processing delays are compounded by the use of automated high speed mail handling machines to keep abreast of the enormous quantity of parcels that the USPS and other entities handle each day. High speed mail handling machines typically utilize pinch rollers to move or guide the parcels. The pinch rollers function in a manner that exerts a squeezing force upon each parcel as the pinch rollers propel or guide the parcel to a desired location.

Therefore, if a parcel that contains contaminant particles is processed by a high speed mail sorting machine that includes pinch rollers, it is likely that the squeezing force of the pinch rollers will eject the contaminant particle. Accordingly, high speed mail handling machines have been identified as a source of aerosol generation, which possibly could aid in the disbursement of threat agents, such as biological or non-biological contaminants, possibly resulting in exposure of USPS personnel and cross-contamination of other parcels that are subsequently processed by the high speed mail handling machine.

A need exists for a conventional high speed mail handling machine that will reduce the likelihood of exposing personnel to contaminants contained within the handled parcels.

A need also exists for a conventional high speed mail handling machine that will detect and identify parcels likely to contain contaminants, allowing the suspect parcel to be further tested.

SUMMARY OF THE INVENTION

The present invention provides an advantage of protecting personnel from contaminated aerosol expelled by the pinch rollers of conventional high speed mail handling machines.

The present invention provides a further advantage of reducing the propagation of such contaminated aerosol beyond the sensing devices of the apparatus of the present invention, thereby reducing potential risk to personnel and potential cross contamination of other parcels.

The present invention provides yet a further advantage of providing real-time screening of parcels sorted by the high speed mail handler to detect possible threat agents, including biological or non-biological contaminants, whether genuine or hoax, which are collectively referred to herein as "contaminants". The screening can be performed either prior to or following irradiation or other parcel sterilization processes.

The screening apparatus of the present invention provides a still further advantage of creating an opening in one or more predetermined positions in each parcel so as to direct the release of any contaminants that may be contained with sealed parcels in a predetermined direction.

The present apparatus provides a further advantage of providing a modified pinch roller assembly that can be integrated with the pinch roller assembly of a conventional high speed mail sorter to create a row of holes along each parcel, which allows for uniform ejection of contaminants in the predetermined direction as the pinch roller compresses the parcel. The predetermined direction is provided by the parcel opener creating the openings in the parcel in one or more predetermined positions.

The present invention provides a still further advantage of providing a puff detector that records and compares a series of digital images taken in the predetermined direction in which the contaminant particles are ejected.

The present invention preferably provides a dwell chamber for reducing the velocity of the air flow extracted from over the compressed, opened parcels, thereby allowing for more accurate sampling by a particulate sampler from a less turbulent environment.

The present invention can be utilized to winnow the number of parcels that must be subjected to irradiation or other sterilization means, thereby accelerating the processing of the parcels.

Further, the present invention allows for timely screening of previously irradiated parcels, wherein such additional screening is useful in detecting parcels containing contaminant residue and hoax threat agents.

The present invention provides a high-speed mail sorting apparatus for automated screening of parcels to identify parcels likely to contain biological or non-biological contaminants, comprising a parcel opener for creating an opening in each parcel, a pinch roller for compressing the opened parcel, an air duct for channeling an air flow over the opened parcel as the opened parcel is compressed, and a particulate sampler for analyzing the air flow to detect whether the opened parcel is likely to contain contaminants.

Another embodiment of the present invention is a high-speed mail sorting apparatus for automated screening of parcels to identify parcels likely to contain biological or non-biological contaminants, comprising a parcel opener for creating an opening in each parcel, a pinch roller for compressing each of a series of opened parcels, an air duct for channeling an air flow over pinch roller as the pinch roller compresses each of the series of opened parcels, and a particulate concentrator for filtering the air flow that is analyzed at periodic intervals to detect whether the series of opened parcel is likely to contain contaminants.

Yet another embodiment of the present invention is a high-speed mail sorting apparatus for automated screening of parcels to identify parcels likely to contain biological or non-biological contaminants, comprising a parcel opener for creating an opening on each parcel in a predetermined position, a pinch roller for compressing each opened parcel and ejecting contaminants from the opened parcel in a predetermined direction, and a puff detector for recording a series of digital images as each opened parcel is compressed, wherein each of the series of digital images is taken in the predetermined direction, and for comparing the series of digital images to determine whether the opened parcel is likely to contain contaminants.

Method for automated screening of parcels sorted by a high speed mail sorting apparatus to identify parcels likely to contain contaminants are also disclosed. One method of the present invention comprises the steps of opening each parcel, utilizing a pinch roller to compress each opened parcel, creating an air flow over the pinch roller, and analyzing the air flow to detect whether the opened parcel is likely to contain contaminants.

BRIEF DESCRIPTION OF THE DRAWINGS

The following detailed description provides a better understanding of the invention as well as other objects and further features thereof, in which reference is made to the accompanying drawings, wherein:

FIG. 5b is a perspective view of the underside of the pinch roller assembly of FIG. 5a.

DETAILED DESCRIPTION OF THE PREFERRED EMBODIMENTS

The following detailed description of the invention is made in reference to the accompanying drawings. In describing the invention, explanation of related functions and constructions that known in the art are omitted for the sake of clearness in understanding the concept of the invention, and to avoid obscuring the invention with unnecessary detail.

Figure 1:
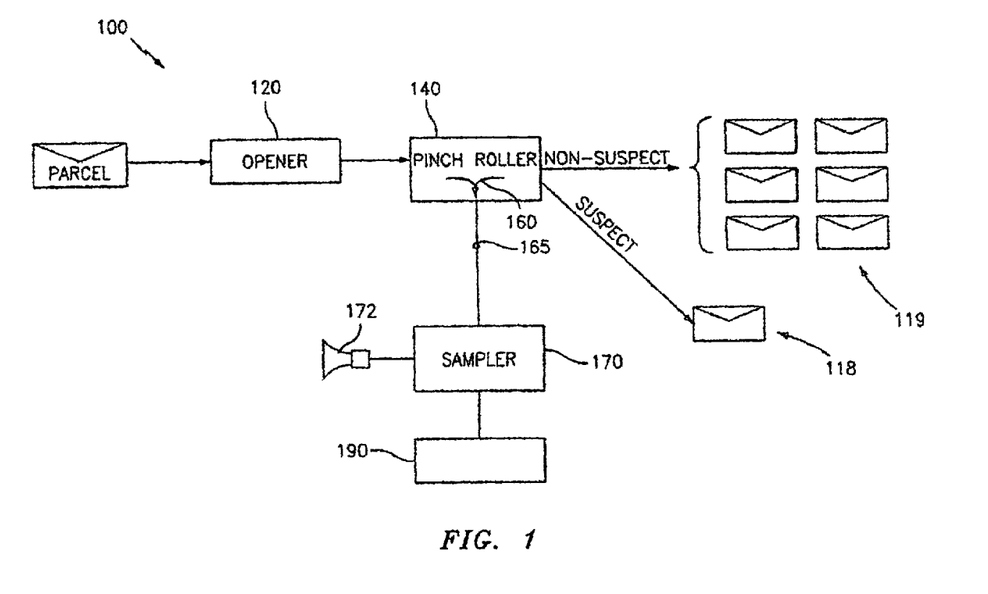
FIG. 1 is a block diagram showing a preferred embodiment of the present invention.

FIG. 1 is a block diagram of a preferred embodiment of the present invention showing the various components of the apparatus 100. The parcels 110, a/k/a media, that can be screened by the apparatus and method of the present invention typically includes, but is not limited to letters, envelopes, magazines, boxes and similar media having an enclosed portion. It is contemplated that media that lack an enclosed portion, e.g. postcards, can also be screened by the apparatus of the present invention. The parcels are, in a preferred embodiment, separated by a separator (not shown) and individually fed into a parcel opener 120.

After parcel opener 120 creates an opening in the parcel 110, parcel 110 is fed into pinch roller 140 of the high speed mail sorting apparatus of the present invention. Pinch roller 140 exerts a squeezing force that compresses each opened parcel 110, causing particles of contaminant contained within the parcel 110 to be substantially ejected through the opening.

An air duct 165 is located near pinch roller 140 for collecting and evacuating particles that are ejected by pinch roller 140. The air duct 165 diverts an airflow 160 collected from over the parcel 110 in the area of the pinch roller 140. In one embodiment, the air duct 165 diverts the airflow 160 toward a particulate sampler 170. Diversion of the air flow 160 from over the compressed parcel 110 reduces the potential that the ejected particles will travel outside of the high speed mail sorting apparatus, possibly reaching USPS personnel. Diversion of the air flow 160, coupled with real-time analysis of the air flow, as explained below, also prevents cross-contamination of other parcels that are subsequently processed by the high speed mail handling machine.

The particulate sampler 170 can utilize one or a combination of detection methods to provide essentially real-time analysis of the air flow 160. The detection methods include, for example, absolute particle count detection, particle size discriminatory detection, particle fluorescence detection and/or particle fluorescence coupled with size detection.

The particulate sampler 170 preferably utilizes a particle counter, such as, for example, that manufactured by Climet Instruments Company and sold under the CLIMET® trademark, to perform the detection of suspect parcels 118. Initial testing revealed that certain parcel types produce high background particle counts. High background and other obscurant aerosols can produce unacceptable false alarms or mask the finding of a contaminated parcel.

Predetermined characteristic signatures of contaminants and hoax particles can also be utilized by the particulate sampler 170, which continuously acquires sensor data from either a single sensor or multiple complementary sensors and correlates the sensor data using a multi-variate analysis scheme.

Figure 2:
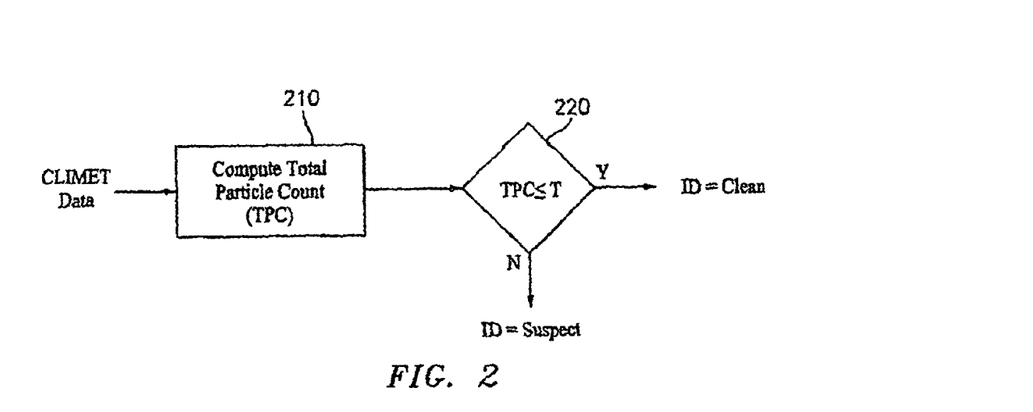
FIG. 2 is a flowchart of a process for performing a total particulate count threshold detection.
Figure 3:
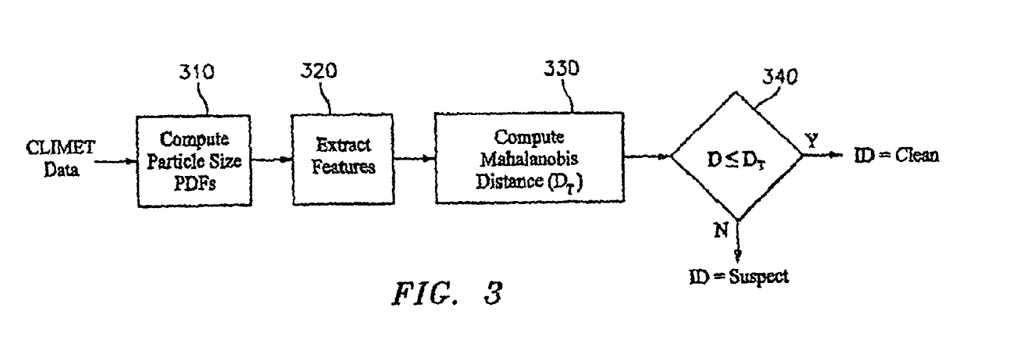
FIG. 3 is a flowchart for performing detection utilizing a Multivariate Gaussian classifier.

A flowchart of a process for performing threshold detection by comparing (in step 220) a total particle count (TPC) computed from the CLiMET data (step 210) with an acceptable threshold (T) is generally described in FIG. 2. Alternatively, or additionally, as generally shown in the flowchart of FIG. 3, an MVG (Multivariate Gaussian) classifier can analyze the CLIMET data. In step 310 the size of the particles in air flow 160 is computed and the features of the particles are extracted (step 320). A Mahalanobis Distance ($D_T$) is then computed (step 330). In step 340, the computed $D_T$ is compared to a previously computed Mahalanobis Distance (D) for clean, non-suspect parcels 119. A determination of whether the parcel 110 is a suspect parcel 118 or a non-suspect parcel 119 can then be made.

The air flow 160 (FIG. 1) is preferably created by a particulate concentrator 190, which is located downstream from the particulate sampler 170, drawing a vacuum on air duct 165, and placing the parcel opener 120 and pinch roller under a negative atmospheric pressure.

A dwell chamber (not shown) is preferably provided along the air duct 165, in a location before the particulate concentrator 190, to slow the velocity of the air flow 160. The dwell chamber, which is located away from pinch roller 140, allows heavier particulates to settle out of the air flow, thereby reducing the number of obscurant aerosol particles, which have been found to typically not be either genuine contaminant or hoax contaminant particles. The dwell chamber allows suspect particles to more evenly distribute in the air flow from which the particulate sampler 170 obtains a sample from the air flow 160 for analysis.

The particulate sampler 170 analyzes the air flow 160 to provide an essentially real-time notification to the operator of the apparatus 100, via an indicator alarm 172, in the event that the air flow 160 is determined to contain either a high concentration of particles or particles having suspect characteristics. Based on the results of its analysis, the particulate sampler 170 provides an output to an alarm indicator 172.

The output to the indicator alarm 172 indicates whether the compressed parcels 110 are non-suspect parcels 119 or suspect parcels 118. For suspect parcels 118, the apparatus is stopped and the suspect parcel 118 is segregated for more detailed confirmatory analysis. Confirmatory analysis includes, but is not limited to, PCR (polymerase chain reaction) analysis. This confirmatory analysis can be performed separately and will not cause delay of the inline, preferably real-time screening process and method of the present invention.

The concentrator 190 preferably can include a screen (not shown) similar to that utilized in a dry-type high efficiency particulate air filter. In this manner, the concentrator 190 captures aerosolized particles ejected by the pinch roller 140. It will be recognized by those of skill in the art that the function of the screens can be performed by other types of confirmatory analysis systems, such as, for example, a liquid or solid sampler unit which collect aerosolized particles, as well as by concentrator units. Also, in certain embodiments known in the art, particulate collectors units can also serve to act as concentrators. Accordingly, the expression "particulate concentrator" as used herein shall be understood to mean concentrators, collectors and units that acts as both concentrators and collectors.

The concentrator 190 is arranged to capture respirable particles, which present research indicates are generally those particles between about 0.3 and about 10 microns in size.

The screens of concentrator 190, which are preferably individually labeled, are analyzed at predetermined periodic intervals to provide a second-check of the accuracy of the analysis performed by the particulate sampler 170. To facilitate the capability of the particulate sampler 170, parcels 110 found to be non-suspect parcels 119 are quarantined in groups corresponding screens which was in place at the time the formerly non-suspect parcels 119 were screened. If the periodic analysis detects contaminants during a time frame when none of the parcels 110 were identified as being suspect parcels 118, the entire quarantined group can either be re-screened or submitted for further testing.

An embedded tracking routine can be included in an alternate embodiment of the present invention to avoid the need for quarantining entire groups or series of parcels. The embedded tracking routine can store image data, such as, for example, data obtained by automated optical character reading procedures. The stored image data can then be correlated to the screens in place when each parcel was processed, and can be utilized to retrieve the now-suspect parcels 118 in the event the analysis detects contaminants not detected by the particulate sampler 170.

The particulate concentrator 190 can be utilized in lieu of the particulate sampler 170 to provide an alternative embodiment of the present invention that will allow evaluation of a series, or batch, of parcels 110. Such embodiment will not, however, provide real-time feedback to the operator as to whether a parcel 110 is either a suspect parcel 118 or a non-suspect parcel 119.

It was observed that the particles ejected by the pinch rollers 140 often form a visible cloud or puff. Therefore, in yet another embodiment, the apparatus of the present invention is arranged to direct the puff in a predetermined direction. Accordingly, a puff detector 180 (not shown), which preferably includes at least a digital camera, is provided to record and compare a series of digital images taken in the predetermined direction of the puff, i.e. the direction in which the contaminant particles are ejected.

The puff detector provides a further mechanism to perform real-time screening, which can be implemented in addition to, or instead of, the particulate sampler 170. The puff detector provides a digital discrete flag upon detection of a particulate cloud that is likely to contain threat material. The puff detector can provide a faster response because, unlike the particulate sampler 170, the puff detector need not have capture an air sample from the air flow 160. Rather, the puff detector compares digital images from the series of digital images taken in the predetermined direction as the parcel 110 is compressed by the pinch roller 140.

The predetermined direction in which the camera of the puff detector is aimed is a predetermined direction that can dynamically vary based on facts that include the thickness of the parcel, the velocity of the parcel, the squeezing force applied by the pinch rollers upon the parcel, than angle of incidence at which the pinch roller is set, the position of the opening that the parcel opener creates in the parcel, whether one or more than one opening or row of openings is created in each parcel, and other factors that may arise in conjunction with the particular high speed sorting apparatus that is utilized with the present invention.

Further, the digital comparison performed by the puff detector can readily be adjust to account for fluctuations in the mail room environment. The digital comparison performed by the puff detector preferably includes the velocity of the air flow 160, the time that it takes to evacuate the air in the vicinity of the pinch roller 140, and the throughput settings of the high speed mail sorting apparatus. Additional characteristics such as, for example, mechanical pressure and angle of incidence at which the pinch roller is set in a specific high speed mail sorting apparatus, can also be input and considered by the puff detector in performing its analysis.

Figure 4:
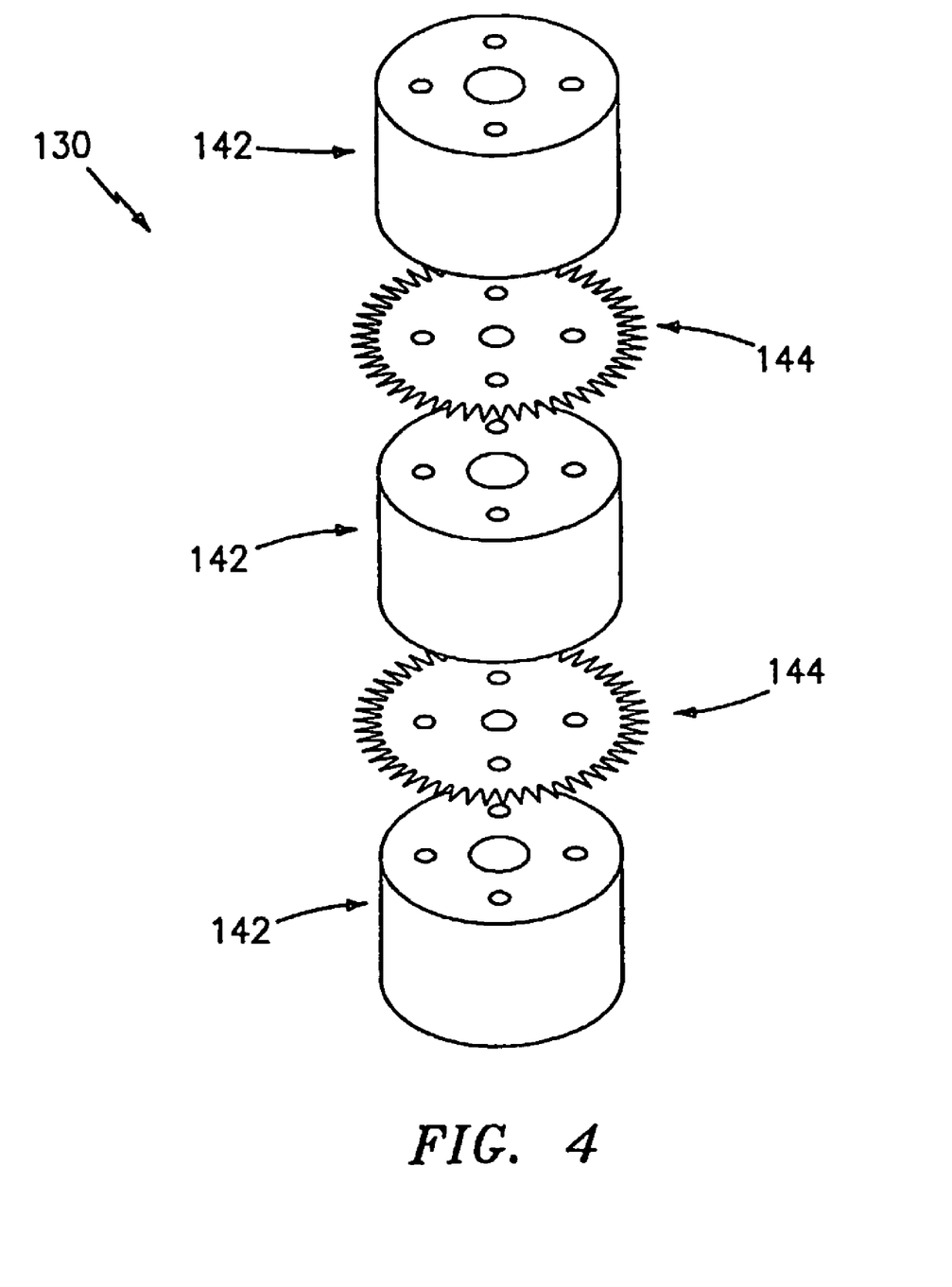
FIG. 4 is a perspective view of a disassembled pinch roller that is integral with a rotary puncher.
Figure 5A:
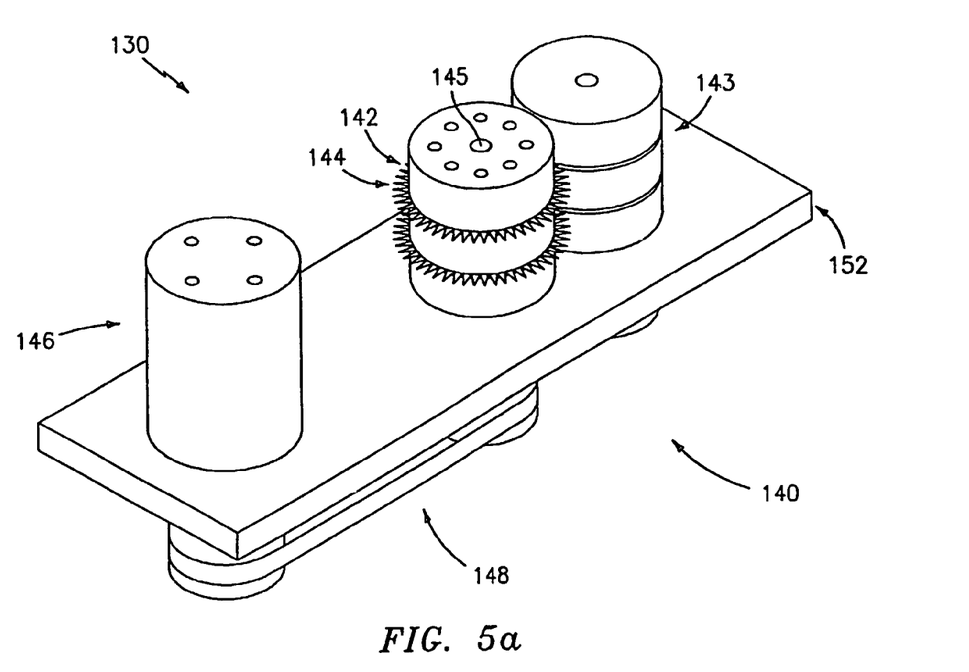
FIG. 5a is a perspective view of a pinch roller assembly of an embodiment of the present invention.
Figure 5B:
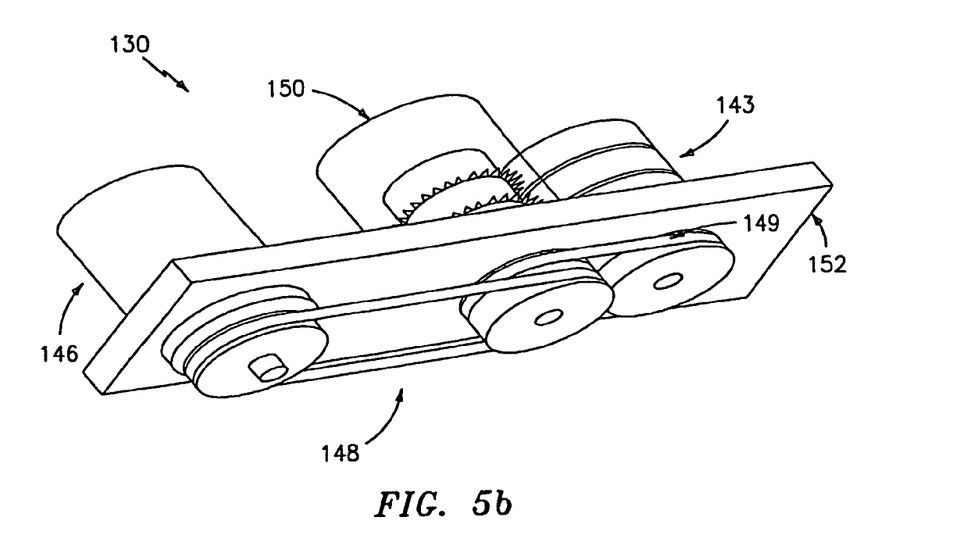
Figure 6:
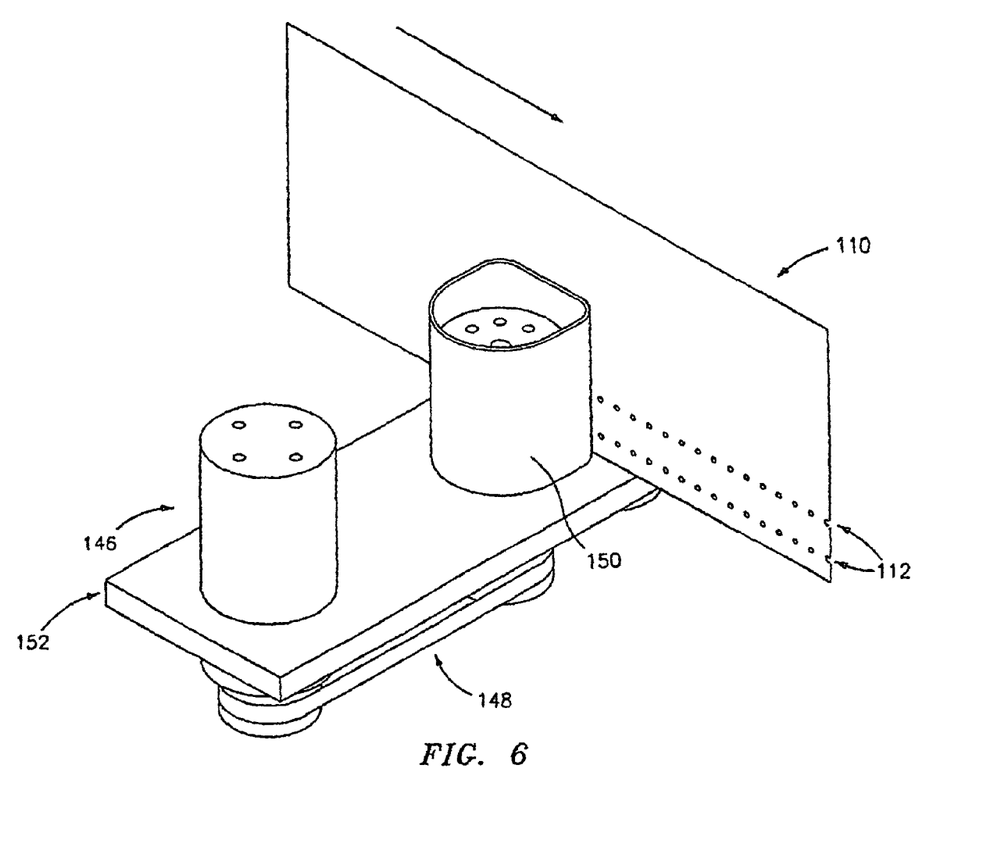
FIG. 6 is a perspective view of showing the parcel in the pinch roller assembly.

The parcel opener 120 can perform its opening function either before or at the pinch roller 140. The parcel opener 120 can be configured as a laser (not shown) or a rotary puncher 130 (FIGS. 4–6). However, other means for opening parcel 100 can be used herein as envisioned by one skilled in the art.

When the parcel opener 120 is configured as a laser, the opening is made in each parcel 110 before the parcel 110 reaches the pinch roller 140. The laser preferably provides at least 48 Joules per square centimeter to drill an opening in the parcel. High speed mail handling machines typically operate at fast, medium or slow speeds, which process ten, five and two or one-half envelopes per second, respectively. With the parcel 110 moving at a processing speed of about two meters per second, a 400 Hz repetition rate can be configured to provide a row of holes in each parcel spaced 0.5 centimeters apart.

FIG. 4–6 provide an example of the parcel opener 120 configured as a rotary puncher 130. FIG. 4 is a perspective view of a disassembled pinch roller 140 that is integrally formed with cutting disks 144 of a rotary puncher 130. In this embodiment, the separate cutting disks 144 are sandwiched between conventional pinch rollers 142, and all are fixed to a shaft 145 (FIG. 5a) to ensure that the pinch rollers 142 and cutting disks 144 rotate at the same rate of speed. The cutting disks 144 shown include a row of spikes that protrude beyond an outer circumference of the pinch rollers 142.

FIG. 5a is an assembled perspective view of the cutting disks 144 integrated with the pinch roller 142 and FIG. 5b is a perspective view of the underside of the pinch roller assembly of FIG. 5a. The shaft 145 extends through a mounting plate 152 for connecting to a belt 148 for driving the integrated pinch roller assembly via a motor 146. An opposing pinch roller 143, which rotates in an opposite direction of the rotary puncher 130 is also preferably provided.

The rotary puncher 130 and the opposing pinch roller 143 can move apart to create a passage therebetween for the parcel 110. A squeezing force resists any separation of the rotary puncher 130 and the opposing pinch roller 143. Mechanisms for creating the squeezing force are well known in the art, and can include springs, pneumatic pressure and elastic tension. A connecting belt 149 is shown in FIG. 5b. The connecting belt 149 has an inherent elasticity, which is utilized to create the elastic tension force for the squeezing force in this embodiment. The embodiment of FIG. 5b utilizes drums that are not affixed and can rotate freely about their respective shafts, thereby utilizing the connecting belt 149 solely to create the elastic force. It will be appreciated that the connecting belt 149 can be utilized, in another embodiment, to drive the rotation of the opposing pinch roller 143.

To protect from inadvertent injury or damage to other components, the spikes of the cutting disks 144 are covered by a guard 150, as generally shown in FIGS. 5b and 6. The guard 150 preferably has a semi-cylindrical shape that is open on the side facing the opposing pinch roller 143. The open portion of the guard 150 exposes the spikes to the parcel 110 when the parcel is inserted between the rotary pincher 130 and the opposing pinch roller 143, as shown in FIG. 6.

FIG. 6 is a perspective view of the pinch roller 140 which also shows the parcel 110 being compressed by the squeezing force and opened by the cutting disks 144. In this embodiment, each of the rotary punchers 144 creates its own row of perforations 112, i.e. a plurality of openings, which are arranged in a row along the parcel 110.

The preferred embodiments that are discussed in detail above each include a parcel opener 120 for creating an opening in each parcel 110. One of skill in the art will recognize that the present invention can be configured in alternative embodiments to screen parcels without the parcel opener 120.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A high-speed mail sorting apparatus for automated screening of parcels to identify parcels likely to contain biological or non-biological contaminants, comprising:
   a parcel opener for creating an opening in each parcel, wherein the opening is created in a predetermined position to eject contaminants from the parcel in a predetermined direction;
   a pinch roller for compressing the opened parcel;
   an air duct for channeling an air flow over the opened parcel as the opened parcel is compressed; and
   a particulate sampler for analyzing the air flow to detect whether the opened parcel is likely to contain contaminants; and
   a puff detector for recording and comparing a series of digital images in the predetermined direction to determine whether the parcel is likely to contain contaminants.

2. A high-speed mail sorting apparatus for automated screening of parcels to identify parcels likely to contain biological or non-biological contaminants, comprising:
   a rotary puncher for creating an opening in each parcel;
   a pinch roller for compressing the opened parcel;
   an air duct for channeling an air flow over the opened parcel as the opened parcel is compressed; and
   a particulate sampler for analyzing the air flow to detect whether the opened parcel is likely to contain contaminants, wherein the rotary puncher comprises a cutting disk which is integral with the pinch roller.

3. The apparatus of claim 2, wherein the cutting disk includes a row of spikes protruding beyond an outer circumference of the pinch roller.

4. The apparatus of claim 3, wherein the rotary puncher creates a plurality of openings in the parcel, wherein the plurality of openings are arranged in a row along the parcel.

5. A high-speed mail sorting apparatus for automated screening of parcels to identify parcels likely to contain biological or non-biological contaminants, comprising:
   a parcel opener for creating an opening on each parcel in a predetermined position;
   a pinch roller for compressing each opened parcel and ejecting contaminants from the opened parcel in a predetermined direction; and
   a puff detector for recording a series of digital images as each opened parcel is compressed, wherein each of the series of digital images is taken in the predetermined direction, and for comparing the series of digital images to determine whether the opened parcel is likely to contain contaminants.

6. A method for automated screening of parcels sorted by a high speed mail sorting apparatus to identify parcels likely to contain contaminants, comprising the steps of:
   opening each parcel;
   utilizing a pinch roller to compress each opened parcel, wherein each parcel is opened by creating a plurality of holes in each parcel in a plurality of predetermined positions and wherein the compressing ejects, in a predetermined direction, contaminants from each parcel;
   creating an air flow over the pinch roller; and
   analyzing the airflow to detect whether the opened parcel is likely to contain contaminants, wherein the analyzing step further includes:
   recording a series of digital images taken in the predetermined direction as the opened parcel is compressed; and
   comparing the series of digital images to determine whether the opened parcel is suspected of containing contaminants.

* * * * *